(12) United States Patent
Fehre et al.

(10) Patent No.: US 7,174,000 B2
(45) Date of Patent: Feb. 6, 2007

(54) METHOD FOR MEASUREMENT OF THE THREE-DIMENSIONAL DENSITY DISTRIBUTION IN BONES

(75) Inventors: Jens Fehre, Hausen (DE); Bernd Granz, Oberasbach (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 18 days.

(21) Appl. No.: 11/182,045

(22) Filed: Jul. 14, 2005

(65) Prior Publication Data

US 2006/0013361 A1    Jan. 19, 2006

(30) Foreign Application Priority Data

Jul. 14, 2004    (DE) .................... 10 2004 033 989

(51) Int. Cl.
*G01B 15/02*    (2006.01)

(52) U.S. Cl. ........................................ 378/54

(58) Field of Classification Search ............ 378/4, 378/19, 50–57, 86–89, 98.8
See application file for complete search history.

(56) References Cited

U.S. PATENT DOCUMENTS

| | | | | |
|---|---|---|---|---|
| 4,721,112 A * | 1/1988 | Hirano et al. | ............... | 600/436 |
| 5,291,537 A * | 3/1994 | Mazess | .................. | 378/54 |
| 5,772,592 A * | 6/1998 | Cheng et al. | ............... | 600/407 |
| 5,774,520 A * | 6/1998 | Bolotin | .................. | 378/50 |
| 5,809,104 A | 9/1998 | Kullenberg et al. | | |
| 6,409,381 B1 | 6/2002 | Siebenhaar et al. | | |
| 6,496,557 B2 * | 12/2002 | Wilson et al. | ............... | 378/21 |
| 6,898,263 B2 | 5/2005 | Avinash et al. | | |
| 2006/0204069 A1 * | 9/2006 | Le Bras et al. | ............... | 382/132 |

OTHER PUBLICATIONS

"Digitale Detektorsysteme für die Projektionsradiographie," Schulz, Fortschr. Röntgenstr., vol. 173 (2001) pp. 1137-1146.
Hologic Brochure for Sahara® Clinical Bone Sonometer (2000).
Enhanced 3-D-Reconstruction Algorithm for C-Arm Systems Suitable for Interventional Procedures, Wiesent et al, IEEE Trans. On Medical Imaging, vol. 19, No. 5 (May 2000), pp. 391-403.
"Improving 3D Image Quality of X-ray C-Arm Imaging Systems by Using Properly Designed Pose Determination Systems for Calibrating the Projection Geometry," Strobel et al, Proc. SPIE, vol. 5030 (2003) pp. 943-954.
Siemens Medical Brochure for SIREMOBIL Iso-$C^{3D}$.
Diagnostic Medical Systems Brochure for UBIS 5000 Ultrasound Bone Imaging Scanner (2003).
"The European Spine Phantom—A Tool for Standardization and Quality Control in Spiral Bone Mineral Measurements by DXA and QCT," Kalender et al, Eur. J. Radiol., vol. 20, No. 2 (1995) pp. 83-92.
AT' syngo Osteo CT Web Page from www.medical.siemens.com.
Diagnostic Medical Systems Brochure for LEXXOS Digital Flash Beam Technology—Bidimensional Densitometer (2003).

* cited by examiner

*Primary Examiner*—Edward J. Glick
*Assistant Examiner*—Irakli Kiknadze
(74) *Attorney, Agent, or Firm*—Schiff Hardin LLP

(57) ABSTRACT

In a method for measurement of the three-dimensional density distribution in a bone, a two-dimensional or three-dimensional image reproducing the quantitative density distribution in the bone is generated using a measurement arrangement that can rotate around an angle of at most 300°.

19 Claims, 1 Drawing Sheet

METHOD FOR MEASUREMENT OF THE THREE-DIMENSIONAL DENSITY DISTRIBUTION IN BONES

BACKGROUND OF THE INVENTION

1. Field of the Invention

The present invention concerns a method for measurement of the three-dimensional density distribution in bones as well as a C-arm x-ray apparatus for such a purpose.

2. Description of the Prior Art

An apparatus for measurement of the mineral content in bones is known from DE 696 20 869 T2 wherein the bones to be examined are successively irradiated with x-ray radiation of different energies. The mineral content in the bones is determined from the measured absorption of the x-ray radiation and using previously acquired reference values acquired by means of a reference subject. As a result, a two-dimensional density distribution is thereby obtained in $g/cm^2$. Under the circumstances, an emerging (i.e., just beginning) variation of the bone density in the bones, in particular a decrease of the mineral content in a predetermined volume element cannot be detected with this known method. For diagnosis of osteoporosis, however, it is extremely important to be able to detect slight changes of the three-dimensional density distribution in the bones at the earliest point in time.

A number of methods for two-dimensional measurement of the bone density are known from the prospect "LEXXOS Digital Flash Beam Technology—Bidimensional Densitomer" published in 2003 by Diagnostic Medical Systems. A two-dimensional digital x-ray image is thereby generated by a linear scan using a single or pencil beam and a linear or punctiform detector. In addition to this, it is also possible to generate a two-dimensional digital x-ray image with a two-dimensionally-expanded x-ray beam and a two-dimensional detector system. A two-dimensional exposure of the entire body can be produced by a movement of the x-ray system relative to the patient bed in the x-direction and y-direction. It is therewith possible to two-dimensionally determine the bone density at selected locations of the acquired area.

For determination of the bone density, from the prospect "UPIS 5000", published in 2003 by Diagnostic Medical Systems, it is also known to measure the bone density by means of ultrasound. Yet a variation of the bone density in a predetermined volume element still cannot be exactly detected.

Determination of the bone density by means of quantitative computed tomography is known from www.syngo.com/deutsch/ct-osteo-htm". A number of slices of a subject, for example of a vertebral body, are thereby acquired. A bone phantom is measured with the acquisition at the same time. As a consequence of this, the quantitative values can be calibrated absolutely (see W. A. Kalender et al., "The European Spine Phantom—a tool for standardization and quality control in spinal bone mineral measurements by DXA and QCT", Eur. J. Radiol., 1995, 20, 2, 83–92). The bone density at specific locations of the spinal column thus can be quantitatively determined.

Furthermore, a mobile x-ray apparatus is known, distributed by the company Siemens AG under the designation "SIREMOBIL Iso-C3D". An x-ray source and a detector for acquisition of two-dimensional x-ray images are provided in opposing arrangement on a C-shaped arc. The x-ray source can be rotated around an isocenter together with the detector. With this known x-ray apparatus, it is possible also to qualitatively, three-dimensionally show a subject to be examined.

SUMMARY OF THE INVENTION

An object of the invention is to provide an optimally precise method for measurement of the three-dimensional density distribution in bones.

This object is achieved according to the invention by a method for measurement of the three-dimensional density distribution in a bone using a measurement arrangement that can rotate around a rotation axis, with an x-ray source and an oppositely-arranged detector with a two-dimensional detector array with a number of detector elements, wherein the bone to be measured is located in the region of the rotation axis, x-ray radiation is generated while rotating the measurement arrangement around the rotation axis by an angle of at least 180° and at most 300°, with the portion of the x-ray radiation not absorbed by the bones being measured by the detector, dependent on the rotation angle of the measurement arrangement. A quantitative density value is calculated for each voxel of an irradiated volume of the bone, and, from the calculated density values, a two-dimensional or three-dimensional image is calculated reproducing the quantitative density distribution in the bones.

With the inventive method, it is possible, in contrast to that prior art, to examine with spatial resolution a predetermined volume in a bone with regard to its density distribution. The measured volume can be determined precisely using the morphology of the bone in its position. As a consequence, it is possible to repeatedly measure the volume over a span of time of multiple years, and to make a conclusion about the course or the beginning of a bone disease from a comparison of the measured values. A significant advantage of the inventive method is that the density distribution in the irradiated (examined) volume can be quantitatively detected immediately with a single measurement, i.e. one rotation around the predetermined rotation angle.

To implement the measurement, the measurement arrangement is appropriately rotated around the rotation axis by an angle of at most 240°, preferably at most 200°. A complete rotation of 360° is not necessary. This presents new freedom in the construction of an apparatus suitable for implementation of the method.

It has proven to be advantageous, dependent on the respective rotation angle, to acquire at least 400 measurement values for each detector element per measurement pass. A "measurement pass", means the acquisition of the measurement values during the rotation of the measurement arrangement. After the acquisition of the measurement values, the measurement arrangement is rotated back again into its initial position. A sufficiently precise conclusion about the density distribution in a bone can be made with the aforementioned number of measurement values. The method can be implemented relatively quickly. With a single measurement pass, a relatively large volume of 10 $cm^3$ to 20 $cm^3$ can be acquired. According to a further embodiment, the x-ray radiation is acquired by the detector elements with a spatial resolution of less than 0.4 mm, preferably with a spatial resolution in the range of 0.1 to 0.2 mm. The density distribution in a predetermined volume in the bone can be determined with an excellent precision.

An iterative algebraic algorithm or an analytical reconstruction method, for example the Feldkamp algorithm for cone beam geometries, can be used for reconstruction of the density distribution. The Feldkamp algorithm is a known method that is in particular used in the field of x-ray computed tomography. For reconstruction of a quantitative density distribution, however, it is necessary to modify the conventional Feldkamp algorithm in a suitable manner. In particular, it is necessary to correct the measured values, preferably using a calibration value. In addition to this, further known correction methods according to the prior art can be used for prevention or suppression of artifacts. Such methods are generally known from the field of image reconstruction in x-ray computed tomography. Thus, for example, reconstruction filters that quantitatively deliver a density value for each voxel can be used for correction. Furthermore, physical effects such as scattered radiation and beam hardening can be corrected. Moreover, a correction of an output intensity can be implemented and/or sectioned projections can be considered. In addition to the density distribution, alternative or additional evaluations can be implemented with regard to the fracture risk, z-score and t-score. Reference is made to the prospect "Sahara Clinical Bone Sensometer", published in 2000 by Hologic, Inc., USA, the contents of which are incorporated herein by reference.

The detector can be fashioned such that the entire volume to be irradiated can be acquired with a single rotation of the measurement arrangement. Furthermore, it has proven to be advantageous to use a detector with a bit depth of at least 12 bits. Conventional detectors can be used for this. It is advantageously not necessary to change the detector in terms of its design for measurement of the density distribution in the bones.

According to a further embodiment, two successive measurement passes can be implemented with different x-ray energies. It is thereby possible to acquire and to show bone portions with different densities in the volume. Reference is made to DE 696 20 869 T2, the content of which is incorporated herein by reference. The second measurement pass using a different x-ray energy can appropriately ensues after rotation of the measurement arrangement back into the initial position. This enables a particularly fast and effective method sequencing.

According to further embodiment, a calibration value can be generated by measurement of a phantom with a known density or density distribution. For example, the phantom can be measured before or during the aforementioned method. It is thus possible to reconstruct the absolute density for each voxel in the reconstructable volume, for example using a cone-beam algorithm.

According to a further embodiment, it is also possible to acquire the calibration value once and then to store it. Multiple measurements of a phantom thus are not necessary.

Furthermore, it has proven to be advantageous to mount the detector in the region of a first end of a carrier and to mount the x-ray source in the region of a second end of the carrier, fashioned in the form of a ring segment and rotatable around the rotation axis. A laminar detector in which the detector elements are arranged in an X/Y plane can be used as the detector. It is also possible to set the rotation plane of the measurement arrangement before the measurement by pivoting on a pivot axis. The inventive method thus can be implemented with a conventional apparatus, for example that of the company Siemens AG under the designation "SIREMOBIL Iso-$C^{3D}$". It is only necessary to install additional software effecting the function of the inventive method. The conventional x-ray apparatus is particularly universal. It is mobile and can be used in the operating room without the patient having to be repositioned. A simplified determination of the mineral content of bones is therewith possible, in particular for bed-ridden patients.

According to a further embodiment of the method, the apparatus is geometrically calibrated with regard to the volume to be measured using previously-acquired measurement values. The calibration can ensue using prominent morphological features of the bone in which the volume to be examined is contained. Previously-stored measurement values can be used to for exact geometric calibration, and using these, for example, a patient bed can automatically be moved relative to the measurement arrangement until the exact position is achieved. The measurement pass can be subsequently implemented with exact geometric calibration.

The measured density distribution in the volume can be subsequently compared by superimposition with an earlier density distribution in the volume. Deviations or differences thus can be immediately, calculationally determined and displayed. A possible bone disease can be quickly and simply detected in this manner.

The superimposition of the measured volumes can ensue using morphological features of the measured bone, or can also ensue using correlations in the measured density distributions.

In the inventive method, the patient remains stationary in he z-direction relative to the rotating measurement arrangement, i.e. the patient is not moved in the z-direction. It is thus possible in a particularly exact manner to repeatedly always measure the same volume. It is also possible, however, to move the patient in the z-direction relative to the measurement arrangement. A number of predetermined volumes thus can be examined in succession.

According to a further embodiment of the invention, a C-arm x-ray apparatus is provided for measurement of the three-dimensional density distribution in a bone. Such a C-arm x-ray apparatus is generally known according to the prior art. For example, reference is made to DE 199 57 330 A1, the disclosure of which is incorporated herein by reference.

If a C-arm x-ray apparatus is used, it should be noted that such an apparatus can exhibit a spatial position inaccuracy in the measurement. The exact geometric arrangement of the x-ray tube, the subject and the detector must be taken into account in the reconstruction for each projection.

DESCRIPTION OF THE PREFERRED EMBODIMENTS

Figure 1:
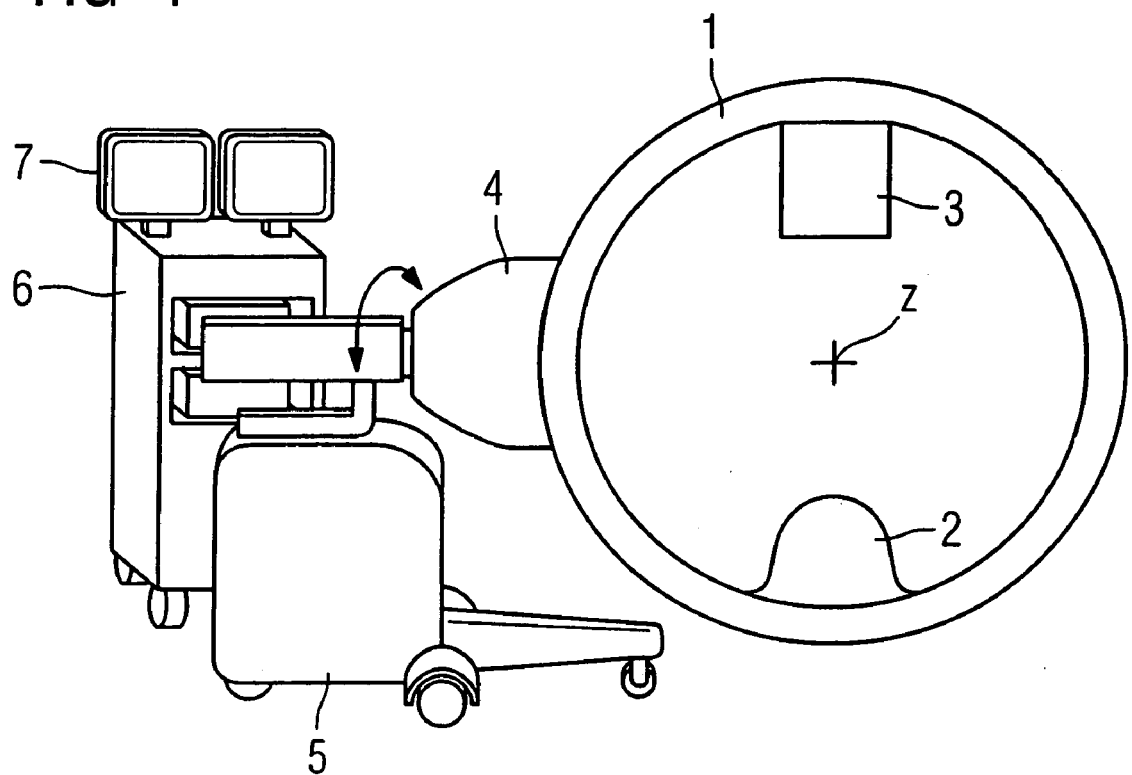
FIG. 1 is a side view of an x-ray apparatus constructed and operating in accordance with the invention.

In FIG. 1, an x-ray source 2 and a detector 3 are mounted in opposing arrangement on a carrier 1 fashioned in the form of an annular segment. The detector 2, for example, can be a planar image detector that has a number of detector elements arranged in an X/Y plane. Naturally, instead of the planar image detector other detectors can also be used. Suitable detectors are known, for example, from R. F. Schulz: RöFo, volume 173, 2001, pages 1137 through 1146. The disclosure of this document is incorporated herein by reference.

The carrier 1 is held on a supporting element 4 such that it can rotate around a z-axis z perpendicular to the plane of the drawing. The supporting element 4 is—as is indicated with the double arrow—mounted on a cart 5 such that it can pivot around a y-axis (not shown here) perpendicular to the z-axis z. A high-voltage generator for generation of the high voltage necessary for the x-ray radiation can be provided in the cart 5. The cart 5 is connected with a mobile element 6 that accommodates evaluation devices such as a computer (not shown here) and a monitor 7.

Figure 2:
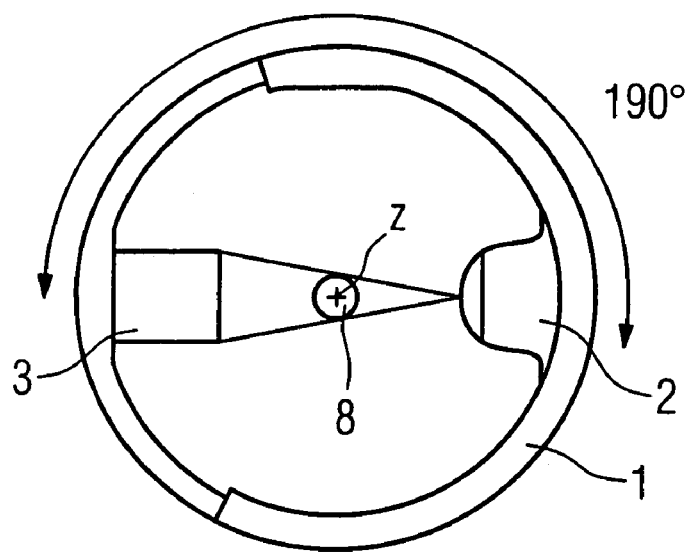
FIG. 2 shows the rotation possibilities of the x-ray apparatus according to FIG. 1.

From FIG. 2 it can be seen that, in the described exemplary embodiment, the carrier 1 can be isocentrically rotated by approximately 190° around the z-axis z. A subject to be examined is designated with the reference character 8 in FIG. 2.

To determine the density distribution in a subject 8 to be examined, i.e. in a bone to be examined, this subject/bone is brought into proximity with the isocenter of the measurement arrangement situated on the z-axis z. The carrier 1 is subsequently moved into an initial position, i.e. rotation angle=0. The carrier 1 is rotated by approximately 190° after the activation of the measurement arrangement. Dependent on the rotation angle, at least 400 two-dimensional absorption distributions are acquired with the detector 3 during the rotation. The measured absorption distributions can be buffered by means of the computer. A density distribution in the examined bone volume is subsequently calculated (for example in the manner of a modified Feldkamp algorithm) from the measured two-dimensional absorption distributions using a previously acquired calibration value.

The determined density distribution can be represented two-dimensionally or three-dimensionally.

In addition to the determined density distribution in the examined volume, geometric features that enable a comparison of the measurement values with future acquired measurement values can be determined and stored. They can be morphological features of the subject 8, or the determined density distribution in the volume itself.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for measuring a three-dimensional density distribution in a bone, comprising the steps of:
    disposing a bone to be measured in a region of a rotational axis of a measurement arrangement having an x-ray source and a two-dimensional radiation detector, disposed substantially opposite said x-ray source, rotatable around said rotational axis;
    irradiating a volume, comprised of voxels, of said bone with x-rays from said x-ray source while rotating said measurement arrangement around said rotational axis through an angle between 180° and 300°, and detecting, with said radiation detector, x-rays attenuated by said bone at a plurality of rotational angles of said measurement arrangement;
    at each of said rotational angles, and for each voxel, electronically calculating a density value dependent on said attenuated x-rays; and
    from said density values, electronically calculating an image of said volume representing a density distribution in said bone in said volume.

2. A method as claimed in claim 1 wherein the step of electronically calculating an image of said volume comprises electronically calculating a two-dimensional image of said volume.

3. A method as claimed in claim 1 wherein the step of electronically calculating an image of said volume comprises electronically calculating a three-dimensional image of said volume.

4. A method as claimed in claim 1 comprising rotating said measurement arrangement through an angle not exceeding 240° while irradiating said volume of said bone with said x-rays from said x-ray source.

5. A method as claimed in claim 1 wherein said radiation detector is a two-dimensional detector array comprised of a plurality of detector elements, and comprising, for each measurement pass for each detector element, obtaining at least 400 measurement values, dependent on the rotational angle, representing said attenuation of said x-rays.

6. A method as claimed in claim 1 wherein said radiation detector is a two-dimensional detector array comprised of a plurality of detector elements, and comprising acquiring said attenuation of said x-rays with said detector elements with a spatial resolution of less than 0.4 mm.

7. A method as claimed in claim 6 comprising acquiring said attenuation of said x-rays with said detector elements with a spatial resolution in a range between 0.1 mm and 0.2 mm.

8. A method as claimed in claim 1 wherein the step of electronically generating an image of said volume comprises reconstructing an image of said volume using an analytical cone-beam algorithm in a computer.

9. A method as claimed in claim 8 comprising employing the Feldkamp algorithm as said cone-beam algorithm.

10. A method as claimed in claim 1 wherein the step of electronically generating an image of said volume comprises reconstructing said image of said volume using an iterative algebraic algorithm.

11. A method as claimed in claim 1 wherein said attenuation of said x-rays at each of said rotational angles represents a projection, and wherein each projection has a projection geometry associated therewith, and wherein the step of electronically generating an image of said volume comprises electronically generating an image of said volume dependent on said attenuation of said x-rays and dependent on the projection geometry for the associated rotation angle.

12. A method as claimed in claim 1 comprising generating measurement values from said radiation detector representing said attenuation by said x-rays, and comprising correcting said measurement values to reduce artifacts in said image.

13. A method as claimed in claim 1 wherein the step of irradiating said volume of said bone comprises irradiating said volume of said bone by rotating said measurement arrangement through two successive measurement passes with said x-ray source emitting x-rays at respectively different energies in said successive measurement passes.

14. A method as claimed in claim 1 comprising generating calibration values by irradiating a phantom disposed in said region of said rotational axis with x-rays from said x-ray source, and wherein the step of electronically generating said image of said volume comprises electronically generating an image of said volume dependent on said attenuation of said x-rays and dependent on said calibration values.

15. A method as claimed in claim 14 comprising electronically storing said calibration values.

16. A method as claimed in claim 1 wherein said measurement arrangement comprises a carrier formed by a ring segment having a first end and a second end, and mounting said x-ray source at said first end of said carrier and mounting said radiation detector at said second end of said carrier, and rotating said carrier around said rotational axis while emitting x-rays from said x-ray source.

17. A method as claimed in claim 1 wherein said rotational axis is substantially parallel to the z-axis of a Cartesian coordinate system, and comprising employing a laminar detector having a plurality of detector elements disposed in an x/y plane of said Cartesian coordinate system as said radiation detector.

18. A method as claimed in claim 1 comprising mounting said measurement arrangement to allow pivoting of said measurement arrangement around a pivot axis and, before irradiating said volume of said bone with said x-rays, selectively pivoting said measurement arrangement around said pivot axis to set a rotation plane of said measurement arrangement.

19. A method as claimed in claim 1 comprising employing a detector with energy resolution as said radiation detector.

\* \* \* \* \*